United States Patent
Matsuura et al.

(10) Patent No.: US 9,693,546 B2
(45) Date of Patent: Jul. 4, 2017

(54) TERMITE EXTERMINATION METHOD AND TERMITE EXTERMINATION DEVICE

(71) Applicant: National University Corporation Okayama University, Okayama (JP)

(72) Inventors: Kenji Matsuura, Kyoto (JP); Chihiro Himuro, Okayama (JP); Tomoyuki Yokoi, Ibaraki (JP); Yuya Suzuki, Hyogo (JP); Kosaku Nozaki, Hyogo (JP); Masanaga Yamaguchi, Hyogo (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 162 days.

(21) Appl. No.: 14/367,563

(22) PCT Filed: Dec. 17, 2012

(86) PCT No.: PCT/JP2012/082687
§ 371 (c)(1),
(2) Date: Jun. 20, 2014

(87) PCT Pub. No.: WO2013/094566
PCT Pub. Date: Jun. 27, 2013

(65) Prior Publication Data
US 2015/0027033 A1 Jan. 29, 2015

(30) Foreign Application Priority Data
Dec. 20, 2011 (JP) ................................. 2011-278361

(51) Int. Cl.
*A01M 1/02* (2006.01)
*A01M 1/20* (2006.01)
(Continued)

(52) U.S. Cl.
CPC ............ *A01M 1/2011* (2013.01); *A01M 1/02* (2013.01); *A01M 1/026* (2013.01);
(Continued)

(58) Field of Classification Search
CPC .......... A01M 1/00; A01M 1/02; A01M 1/026; A01M 1/20; A01M 1/2005; A01M 1/2011; A01M 17/00
(Continued)

(56) References Cited

U.S. PATENT DOCUMENTS 4,043,073 A * 8/1977 Basile ...................... A01M 1/02
43/132.1
5,778,596 A * 7/1998 Henderson ........... A01M 1/2011
43/132.1
(Continued)

FOREIGN PATENT DOCUMENTS

EP 1489903 A1 12/2004
JP 10265315 A 10/1998
(Continued)

OTHER PUBLICATIONS

International Search Report for PCT/JP2012/082687 dated Mar. 12, 2013.
(Continued)

*Primary Examiner* — Darren W Ark
(74) *Attorney, Agent, or Firm* — Millen, White, Zelano & Branigan, P.C.; William Nixon

(57) ABSTRACT

A termite extermination method of the present invention includes putting a termite extermination device 1 at a termite habitat. The termite extermination device 1 includes an exterminating agent housing 3 that is at least partially formed of a moisture-proof film 12 and houses an exterminating agent 13 in an interior of the exterminating agent housing 3. The moisture-proof film 12 includes a laminate
(Continued)

having a paper layer and a metal layer laminated one upon another. At least the paper layer is subjected to a rugging process. The laminate is disposed in the exterminating agent housing 3 so that the paper layer serves as an outermost surface.

7 Claims, 5 Drawing Sheets

(51) Int. Cl.
  *A01M 17/00* (2006.01)
  *A01N 25/34* (2006.01)
(52) U.S. Cl.
  CPC ........ *A01M 1/2005* (2013.01); *A01M 1/2016* (2013.01); *A01M 17/00* (2013.01); *A01N 25/34* (2013.01)
(58) Field of Classification Search
  USPC ........................................ 43/132.1, 131, 124
  See application file for complete search history.

(56) References Cited

U.S. PATENT DOCUMENTS

| | | | | |
|---|---|---|---|---|
| 5,810,312 | A * | 9/1998 | Perlman | B01L 9/00 43/114 |
| 6,079,150 | A * | 6/2000 | Setikas | A01M 1/026 43/131 |
| 6,219,961 | B1 * | 4/2001 | Ballard | A01M 1/026 43/131 |
| 6,505,434 | B1 * | 1/2003 | Kloczko | A01M 1/14 43/114 |
| 6,581,325 | B2 * | 6/2003 | Gordon | A01M 1/2005 43/132.1 |
| 6,584,728 | B2 * | 7/2003 | Aesch, Jr. | A01M 1/026 43/132.1 |
| 6,606,816 | B2 * | 8/2003 | Oi | A01M 1/026 43/132.1 |
| 6,681,518 | B2 * | 1/2004 | Aesch, Jr. | A01M 1/026 43/132.1 |
| 6,729,067 | B2 * | 5/2004 | Lund | A01M 1/026 43/132.1 |
| 6,803,051 | B1 * | 10/2004 | Voris | A01N 25/12 424/403 |
| 6,857,223 | B2 * | 2/2005 | Su | A01M 1/2005 43/131 |
| 7,335,374 | B2 * | 2/2008 | Voris | A01N 25/12 424/405 |
| 7,434,351 | B2 * | 10/2008 | Bette | A01M 1/106 43/131 |
| 8,196,342 | B2 * | 6/2012 | Tolley | A01M 1/026 43/132.1 |
| 8,454,985 | B2 * | 6/2013 | Eger, Jr. | A01M 1/026 424/405 |
| 8,753,658 | B2 * | 6/2014 | Eger, Jr. | A01M 1/026 424/405 |
| 8,832,994 | B2 * | 9/2014 | Tolley | A01M 1/026 43/132.1 |
| 2003/0177689 | A1 | 9/2003 | Su | |
| 2004/0031190 | A1 * | 2/2004 | Collins | A01M 1/026 43/132.1 |
| 2004/0062747 | A1 * | 4/2004 | Palmere | A01N 59/14 424/78.38 |
| 2006/0016121 | A1 * | 1/2006 | Ballard | A01M 1/026 43/132.1 |
| 2006/0162236 | A1 * | 7/2006 | French | A01M 1/026 43/132.1 |
| 2006/0254123 | A1 * | 11/2006 | Su | A01M 1/026 43/132.1 |
| 2007/0256350 | A1 * | 11/2007 | Cates | A01M 1/026 43/132.1 |
| 2010/0158965 | A1 * | 6/2010 | Beitzel | A01N 25/34 43/132.1 |
| 2013/0276352 | A1 * | 10/2013 | Eger, Jr. | A01M 1/026 424/410 |
| 2013/0276354 | A1 * | 10/2013 | Eger, Jr. | A01M 1/026 43/131 |
| 2013/0340321 | A1 * | 12/2013 | de Lame | A01M 1/2005 43/131 |
| 2015/0020439 | A1 * | 1/2015 | Willenberg | A01M 1/2055 43/132.1 |
| 2015/0272109 | A1 * | 10/2015 | Davis | A01M 29/12 43/131 |

FOREIGN PATENT DOCUMENTS

| | | | | |
|---|---|---|---|---|
| JP | 11127753 | A * | 5/1999 | |
| JP | 11343202 | A | 12/1999 | |
| JP | 2004107215 | A | 4/2004 | |
| JP | 2004137150 | A | 5/2004 | |
| JP | 2005520563 | A | 7/2005 | |
| JP | 2009178116 | A | 8/2009 | |
| WO | 03082000 | A1 | 10/2003 | |
| WO | WO 03082000 | A1 * | 10/2003 | ......... A01M 1/2005 |
| WO | 2013094566 | A1 | 6/2013 | |

OTHER PUBLICATIONS

English Abstract of JP-10-265315, Publication Date: Oct. 16, 1998.
English Abstract of JP-11-127753, Publication Date: May 18, 1999.
English Abstract of JP-11-343202, Publication Date: Dec. 14, 1999.
English Abstract of JP-2004-107215, Publication Date: Apr. 8, 2004.
English Abstract of JP-2004-137150, Publication Date: May 13, 2004.
English Abstract of JP-2009-178116, Publication Date: Aug. 9, 2013.
English Abstract of WO-2013-094566, Publication Date: Jun. 27, 2013.

* cited by examiner

Fig. 4
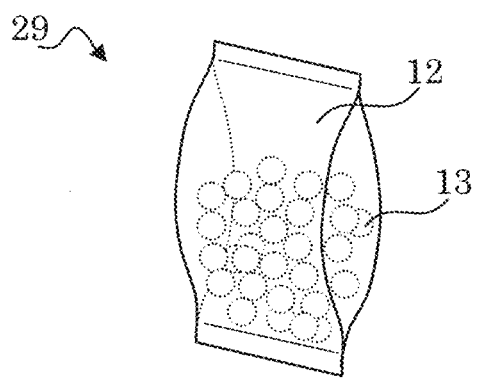
Fig. 5(a)  Fig. 5(b)  Fig. 5(c)  Fig. 5(d)
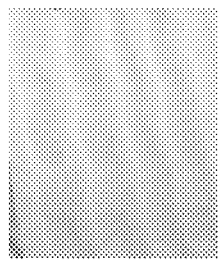 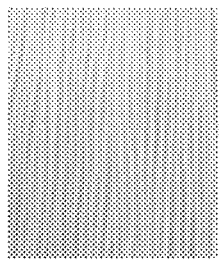 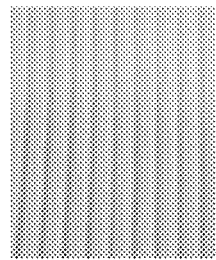 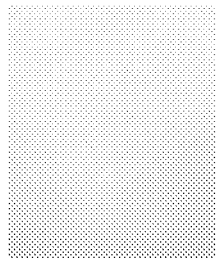
Fig. 6
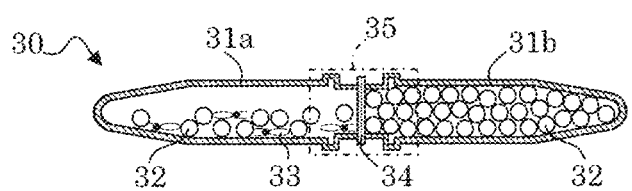

The parts surrounded by the black lines are the penetration parts
(one of the penetration parts is indicated by an arrow).

TERMITE EXTERMINATION METHOD AND TERMITE EXTERMINATION DEVICE

TECHNICAL FIELD

The present invention relates to a termite extermination method and a termite extermination device.

BACKGROUND ART

When an exterminating agent, such as a poison bait and an insecticide, is used for termite extermination, it is desirable to put the exterminating agent, for example, in the ground including a termite habitat. However, when the exterminating agent is put as it is in the ground, there has been the problem that the exterminating agent becomes moldy depending on moisture, and temperature and humidity conditions, thus causing, for example, deactivation of termite extermination effect.

Therefore, considerations have conventionally been made for preventing the deactivation of the termite extermination effect depending on moisture, and temperature and humidity conditions. For example, patent document 1 discloses a termite extermination member in which at least part of a poison bait is coated with a moisture-proof film formed of thermosetting plastic. Patent document 2 discloses a termite exterminating agent in which a poison bait is sealed in a band-shaped container formed of a moisture-proof material having a paper layer and a thermosetting resin film layer laminated one upon another. Patent document 3 discloses an ant-proof material in which a poison bait is sealed in a resin container formed of polystyrene foam and/or urethane foam that has poor water permeability and is susceptible to feeding damage by termites.

However, the resin film and the resin container disclosed in the patent documents 1 to 3 have insufficient moisture proofness and are less attractive to termites.

As a container or sheet attractive to termites, a cellulous sheet having a single-faced corrugated board disposed on a surface thereof (refer to patent document 4), and a sheet (refer to patent document 5) have been disclosed. The latter sheet is obtained by integrally molding a pulp mold having a rough surface, such as a decayed wood, together with a cellulous-based material, and a synthetic resin. However, even the sheet or the resin container is less attractive to termites, and it is therefore difficult to allow the termites to pass through the sheet or the resin container. Additionally, the sheet and the resin container have insufficient moisture proofness.

RELATED ART DOCUMENTS

Patent Documents

Patent Document 1: Japanese Unexamined Patent Publication No. 2004-107215
Patent Document 2: Japanese Unexamined Patent Publication No. 11-127753
Patent Document 3: Japanese Unexamined Patent Publication No. 2004-137150
Patent Document 4: Japanese Unexamined Patent Publication No. 10-265315
Patent Document 5: Japanese Unexamined Patent Publication No. 2009-178116

SUMMARY OF THE INVENTION

Problems to be Solved by the Invention

It is an object of the present invention to provide a termite extermination method capable of suppressing the deactivation of termite extermination effect of an exterminating agent due to moisture, and temperature and humidity conditions so as to efficiently exterminate termites, as well as a termite extermination device for use in the termite extermination method.

Means for Solving the Problem

The present inventors completed the present invention through intense research in a solution to the problem.

That is, the termite extermination method and the termite extermination device of the present invention include the following aspects.

According to a first aspect of the present invention, there is provided a termite extermination method including putting a termite extermination device at a termite habitat. The termite extermination device includes an exterminating agent housing that is at least partially formed of a moisture-proof film and houses an exterminating agent in an interior of the exterminating agent housing. The moisture-proof film includes a laminate having a paper layer and a metal layer laminated one upon another. At least the paper layer is subjected to a rugging process. The laminate is disposed in the exterminating agent housing so that the paper layer serves as an outermost surface.

According to a second aspect of the present invention, there is provided the termite extermination method according to the first aspect in which the moisture-proof film is a laminate having a synthetic resin layer.

According to a third aspect of the present invention, there is provided the termite extermination method according to the first or second aspect in which the moisture-proof film includes a paper layer, a synthetic resin layer (A), a metal layer, and a synthetic resin layer (B) laminated one upon another in an order named.

According to a fourth aspect of the present invention, there is provided the termite extermination method according to the third aspect in which at least one of the synthetic resin layer (A) and the synthetic resin layer (B) is a hardly-stretchable resin film.

According to a fifth aspect of the present invention, there is provided the termite extermination method according to any one of the first to fourth aspects in which the exterminating agent housing is disposed adjacent to an attractant housing that houses therein a termite attractant and in which the moisture-proof film in the exterminating agent housing faces to the attractant housing.

According to a sixth aspect of the present invention, there is provided a termite extermination device for use in the termite extermination method according to any one of the first to fifth aspects. The termite extermination device includes an exterminating agent housing that is at least partially formed of a moisture-proof film and houses an exterminating agent in an interior of the exterminating agent housing. The moisture-proof film includes a laminate having a paper layer and a metal layer laminated one upon another. At least the paper layer is subjected to a rugging process. The laminate is disposed in the exterminating agent housing so that the paper layer serves as an outermost surface.

Effect of the Invention

The termite extermination method of the present invention uses the termite extermination device at least partially formed of the moisture-proof film including the metal layer. This ensures high moisture proofness so as to suppress, for example, the deactivation of termite extermination effect even when the termite extermination device is put under a high-humidity environment. Further, the moisture-proof film is attractive to termites because the paper layer subjected to the rugging process is disposed on the outermost surface of the exterminating agent housing. This makes it easier for the termites to chew up the moisture-proof film and enter the exterminating agent housing that houses therein the exterminating agent. Efficient termite extermination is ensured by putting the termite extermination device at the termite habitat.

BRIEF DESCRIPTION OF THE DRAWINGS

FIG. 4 is a perspective view showing another embodiment of an exterminating agent housing in the present invention;

FIGS. 5(a) to 5(d) are reference photographs of sample films subjected to a rugging process used for chewing tests and field tests, specifically, FIG. 5(a) is a sample film subjected to a wrinkle-type rugging process, FIG. 5(b) is a sample film subjected to an A-type rugging process, FIG. 5(c) is a sample film subjected to a B-type rugging process, and FIG. 5(d) is a sample film provided with a rugged surface shape of approximately 0.1 mm by an embossing process;

FIG. 6 is a cross-sectional view of a test container used for a chewing test I;

PREFERRED EMBODIMENTS FOR CARRYING OUT THE INVENTION

A termite extermination method of the present invention includes putting, at a termite habitat, a termite extermination device including an exterminating agent housing that is at least partially formed of a predetermined moisture-proof film and houses an exterminating agent in the exterminating agent housing. Hereinafter, the term "termite habitat" denotes a place where the presence of termites or a living trace of termites is observed, such as an termite hill and surroundings thereof, and termite passages and surroundings thereof, and a place to prevent or control termite activity and surroundings thereof.

Extermination targets of the present invention are all kinds of termites, including not only native termites, but also invasive termites. Examples of the native termites include Rhinotermitidae such as *Coptotermes formosanus* and *Reticulitermes speratus*, *Cryptotermes*, Kalotermitidae such as *Glyptotermes satsumensis*, Termitidae such as *Nasutitermes takasagoensis* and *Odontotermes formosanus*, and Termopsidae such as *Hodotermopsis sjostedti*. Examples of the invasive termites include *Incisitermes minor*.

(Embodiment of Termite Extermination Device)

Figure 1A:
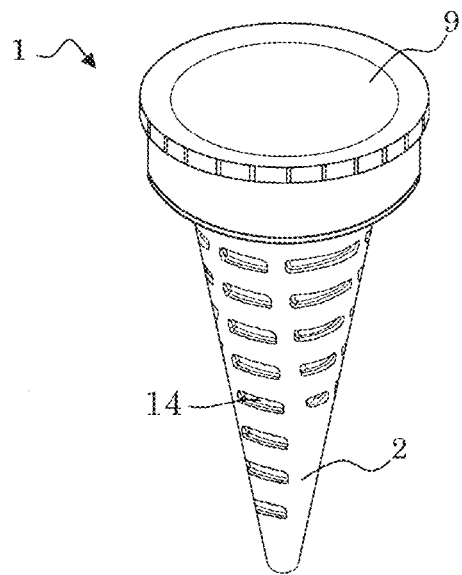
FIG. 1(a) is a perspective view showing an embodiment of a termite extermination device of the present invention.
Figure 1B:
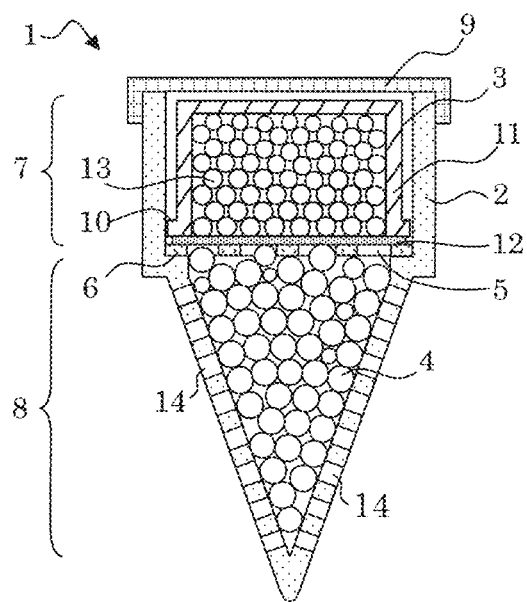
FIG. 1(b) is a cross-sectional view of the termite extermination device.

FIG. 1(a) is a perspective view showing an embodiment of a termite extermination device 1 of the present invention. FIG. 1(b) is a cross-sectional view of the termite extermination device 1.

The termite extermination device 1 includes a stake-type attractant housing 2, and an exterminating agent housing 3 and a termite attractant 4 that are housed in the interior of the attractant housing 2. As shown in FIG. 1(b), the interior of the attractant housing 2 is divided into an upper part and a lower part by a partition plate 6 with a termite invasion port 5. The upper part is an exterminating agent storage part 7 (exterminating agent storage space), and the lower part is an attractant storage part 8 (attractant storage space).

That is, the exterminating agent housing 3 is housed in the exterminating agent storage part 7 within the attractant housing 2. The termite attractant 4 is housed in the attractant storage part 8. An overcap 9 is secured to a top portion of the attractant housing 2.

The termite extermination device 1 includes the stake-type attractant housing 2 and hence is effective in exterminating termites living in a deep underground colony.

(Attractant Housing)

The material of the attractant housing 2 is not particularly limited. Materials highly resistant to deterioration in the ground are suitable. Examples of the materials include polyesters such as polyethylene, polypropylene, and polyethylene terephthalate, synthetic resins such as polystyrene, polycarbonate, Polyacrylate, and polyacrylonitrile, glass, earthenware, metals, and ceramic. The material of the attractant housing 2 is preferably a transparent or semitransparent material from the viewpoint of checking the situation in the interior of the attractant housing 2. Among others, polyesters such as polyethylene, polypropylene, and polyethylene terephthalate, polystyrene, polycarbonate, Polyacrylate, polyacrylonitrile, and glass are preferable.

Although not shown, an outer surface of the attractant housing 2 in the attractant storage part 8 preferably has a screw shape. This ensures that the termite extermination device 1 is screwed into the ground when the termite extermination device 1 is put in the ground. Thus, the termite extermination device 1 can easily be put in the ground and is easy to use.

(Exterminating Agent Housing)

The exterminating agent housing 3 includes a cup-type exterminating agent storage container 11, a moisture-proof film 12, and an exterminating agent 13. The exterminating agent storage container 11 has an opening that permits invasion of termites and has a flange part 10 along an outer peripheral edge of the opening. The moisture-proof film 12 is adhered to the flange part 10 so as to fully close the opening. The exterminating agent 13 is stored in a sealed space defined by the exterminating agent storage container 11 and the moisture-proof film 12. Further, the moisture-proof film 12 is disposed so as to face to the attractant storage part 8 as shown in FIG. 1(b). Thus, the moisture-proof film 12 facing to the attractant storage part 8 makes it easier for termites to bite the moisture-proof film 12. Additionally, the exterminating agent 13 is sealed by the exterminating agent storage container 11 and the moisture-proof film 12, and other pests, such as ants, may not bite the moisture-proof film 12 and break the moisture-proof film 12. Consequently, it is difficult for other pests to access to the exterminating agent 13, while allowing termites to selectively access to the exterminating agent 13.

The material of the exterminating agent storage container 11 is not particularly limited as long as having excellent moisture proofness. Materials highly resistant to deterioration in the ground are suitable. Examples of the materials include polyesters such as polyethylene, polypropylene, and polyethylene terephthalate, synthetic resins such as polystyrene, polycarbonate, Polyacrylate, and polyacrylonitrile, glass, earthenware, metals, and ceramic. The material of the exterminating agent storage container 11 is preferably a transparent or semitransparent material from the viewpoint of checking the situation in the interior of the exterminating agent housing 3. Among others, polyesters such as polyethylene, polypropylene, and polyethylene terephthalate, polystyrene, polycarbonate, Polyacrylate, polyacrylonitrile, and glass are preferable.

The shape (cup cross-sectional shape) of the exterminating agent storage container 11 is not particularly limited. The exterminating agent storage container 11 may have a round shape, or a corner type such as a square shape. An internal volume of the exterminating agent storage container 11 is preferably approximately 2 to 200 ml in order to facilitate burying in the ground.

A method for adhering the exterminating agent storage container 11 and the moisture-proof film 12 to each other is not particularly limited. For example, well-known adhesive may be used. Alternatively, heat fusion may be employed according to the material of the exterminating agent storage container 11 and the moisture-proof film 12.

(Moisture-Proof Film)

The moisture-proof film 12 is a laminate having a paper layer and a metal layer laminated one upon another, and has excellent moisture proofness. Owing to the moisture proofness, the exterminating agent 13 housed in the exterminating agent housing 3 using the moisture-proof film 12 is unsusceptible to the influences of moisture and rainwater in the ground, and the exterminating agent 13 can be kept dry. Hence, even when the termite extermination device 1 is put under a high-humidity environment comfortable for termites, it is possible to suppress, for example, the deactivation of termite extermination effect of the exterminating agent 13 due to fungal growth. That is, the extermination efficiency of the exterminating agent 13 to be used does not deteriorate, thus ensuring the efficient termite extermination. The moisture-proof film 12 can also be made easily attachable to the exterminating agent storage container 11. Further, the exterminating agent 13 is sealed by the exterminating agent storage container 11 and the moisture-proof film 12. This configuration ensures that the exterminating agent is efficiently used for termite extermination while eliminating the probability that pests other than termites, such as ants, impair sealing properties and cause the deactivation of termite extermination effect of the exterminating agent, or other pests consume the exterminating agent.

The moisture-proof film 12 preferably has a thickness of 5 to 500 μm, more preferably 5 to 200 μm. When the moisture-proof film 12 has a thickness exceeding 500 μm, it may be difficult for termites to chew up the moisture-proof film, or it may take a lot of time before termites chew up the moisture-proof film, failing to efficiently exterminate the termites. When the moisture-proof film 12 has a thickness of less than 5 μm, the moisture proofness and mechanical strength of the moisture-proof film may be insufficient.

The moisture-proof film 12 is subjected to a rugging process. This improves attractiveness to termites so as to allow them to chew up the moisture-proof film and achieve considerable reduction of the time required for chewing up. This further allows the termites to enter the exterminating agent storage container 11 so as to efficiently exterminate the termites. In the case of the moisture-proof film not subjected to the rugging process, termites cannot chew up the moisture-proof film. Hence, it is difficult to exterminate the termites.

The rugged surface shape may be random or regular. The rugged surface needs to have such a size to make it easier for termites to bite. For example, the height of protrusions is approximately 0.05 to 5 mm, preferably 0.1 to 1 mm. The width of the protrusions is approximately 0.1 to 10 mm, preferably 0.5 to 5 mm.

The rugging process needs to be applied to at least the paper layer disposed on the outermost surface of the exterminating agent housing 3 in the moisture-proof film 12. Alternatively, the rugging process may be applied to all the layers of the moisture-proof film 12.

Examples of the rugging process include embossing process, wrinkle process, calendar process, wave process, pleat process, and surface texturing. The rugging process may suitably be selected from among these processes according to a desired rugged surface shape. Particularly, the rugging process is preferably an embossing process or wrinkle process in order to make it easier to manufacture the moisture-proof film and make it easier for termites to chew up.

The structure of the moisture-proof film 12 is not particularly limited as long as the outermost surface is the paper layer. For example, a two-layer structure of paper/metal, or structures made up of three or more layers, such as paper/metal/paper and paper/metal/paper/metal, may be employed. Hereinafter, for example, the term "paper/metal/paper/metal" denotes the moisture-proof film in which the paper layer, the metal layer, the paper layer, and the metal layer are laminated in the order named.

The moisture-proof film 12 may be a laminate further including a synthetic resin layer. It is consequently ensured to suppress breakage of the metal layer and improve the moisture proofness and processing suitability (sealing properties) of the moisture-proof film 12 when the moisture-proof film 12 is manufactured by laminating the laminates.

The structure of the moisture-proof film 12 including the synthetic resin layer is not particularly limited as long as the paper layer, the synthetic resin layer, and the metal layer are included and at least one of surfaces (outermost surfaces) is the paper layer. Examples of the structure of the moisture-proof film 12 include paper/synthetic resin (A)/metal/synthetic resin (B), paper/synthetic resin/metal, paper/metal/synthetic resin, and paper/metal/synthetic resin/paper. Among others, paper/synthetic resin (A)/metal/synthetic resin (B) is preferred from the viewpoints of excellent moisture proofness and mechanical strength. The lamination of the synthetic resin layer (A) or (B) on the front and back surfaces of the metal layer prevents breakage of the metal layer and minimizes the phenomenon that the moisture-proof film 12 is exposed to moisture. The synthetic resin layer (A) and the synthetic resin layer (B) may be composed of an identical synthetic resin, or different resins. Alternatively, both synthetic resin layers may be a laminate of synthetic resin layers composed of a plurality of materials. The individual layers in the moisture-proof film 12 may be laminated one upon another with well-known adhesive interposed therebetween.

(Paper Layer)

The moisture-proof film 12 includes a paper layer that makes it easier for termites to bite. Therefore, the moisture-proof film is arranged so that the paper layer is disposed outside the exterminating agent housing 3.

The paper layer is not particularly limited. Examples of the paper layer include simili paper, wood-free paper, kraft paper, machine glazed poster paper, tissue paper, glassine paper, Japanese paper, carton, and corrugated board.

The paper layer has a weighing of 10 to 1000 g/m², preferably 20 to 500 g/m².

(Synthetic Resin Layer)

Examples of the synthetic resin layer include hardly-stretchable resin films such as polyethylene terephthalate (PET), polyethylene (PE), ethylene acrylic acid copolymer (EAA), polypropylene (PP), ethylene vinyl alcohol copolymer (EVOH), ethylene vinyl acetate copolymer (EVA), polyacrylonitrile (PAN), nylon, vinyl ester, polyimide (PI), polybenzimidazole (PBI), and poly(methyl methacrylate) (PMMA). One kind or two or more kinds of these may be used by laminating them one upon another. Particularly, PE has the function of serving as adhesive between the paper layer and the metal layer by performing, for example, thermocompression bonding when manufacturing the moisture-proof film having the structure of paper/PE/metal.

The synthetic resin layer has a thickness of 10 to 1000 µm, preferably 15 to 150 µm.

When the structure of the moisture-proof film 12 is the paper/synthetic resin (A)/metal/synthetic resin (B), at least one of the synthetic resin layers (A) and (B) preferably includes the hardly-stretchable resin. This ensures effective suppression of breakage of the metal layer when the moisture-proof film 12 is subjected to the rugging process.

The hardly-stretchable resin film is not particularly limited as long as being resin that hardly stretches during the rugging process of the moisture-proof film and capable of preventing the breakage of the metal layer. Examples of the hardly-stretchable resin film include a polyethylene terephthalate (PET) film, a polystyrene (PS) film, a polyacrylonitrile (PAN) film, a nylon film, a vinyl ester film, a polyimide (PI) film, a polybenzimidazole (PBI) film, and a poly(methyl methacrylate) (PMMA) film. Particularly, the hardly-stretchable resin film is preferably the PET film because it hardly stretches during the rugging process and is capable of preventing the breakage of the metal layer.

Particularly, in the case of the moisture-proof film having the structure of the paper/synthetic resin (A)/metal/synthetic resin (B), the synthetic resin (A) is preferably PE and the synthetic resin (B) is preferably PET/CPP. With this structure, the PE of the synthetic resin (A) serves as an adhesive layer in an extrusion lamination method, and the PET of the synthetic resin (B) prevents the breakage of the metal layer during the rugging process, and the CPP is usable as a sealant with respect to the exterminating agent storage container 11. The term "CPP" denotes cast polypropylene.

(Metal Layer)

The moisture-proof film 12 includes a metal layer that is particularly excellent in moisture proofness. Termites usually do not bite and do not chew up metal. However, it is possible to allow termites to chew up the metal layer by performing the rugging process in combination with the paper layer. That is, it is ensured to obtain a novel moisture-proof film that is particularly excellent in moisture proofness and can be chewed by termites.

Examples of the metal layer include gold, silver, aluminum, and iron. Particularly, the metal layer is preferably an aluminum layer from the viewpoints of a tendency to be easily chewed up by termites, as well as moisture proofness and processing suitability. It is also possible to use one obtained by depositing the metal layer.

Examples of the aluminum layer include aluminum foil, and ones obtained by depositing aluminum on a paper or synthetic resin.

The metal layer has a thickness of 1 to 40 µm, preferably 5 to 20 µm. In the case of depositing metal, the metal layer has a thickness of 0.01 to 1 µm, preferably 0.02 to 0.2 µm.

As a method for manufacturing the moisture-proof film 12 by laminating the paper layer, the synthetic resin layer, and the metal layer, there are well-known methods, such as extrusion lamination method, dry lamination method, wet lamination method, and hot melt lamination method.

As adhesive used for lamination, well-known adhesive may be used.

(Termite Exterminating Agent)

The termite exterminating agent 13 is a mixture of an effective ingredient for termite extermination and a base material for impregnating the effective ingredient. As the base material, there are ones that the type of termites as a termination target like to feed, which are described later as a termite attractant, and carriable ones that termites carry them back to their colony.

As an effective ingredient for termite extermination, ingredients conventionally used for termite extermination are usable, and slow-acting ones are particularly preferable. This is because the effective ingredient for termite extermination can be spread over the entire colony so as to effectively exterminate termites by allowing the exterminating agent 13 taken into the bodies of the termites to be carried back to their colony, or by allowing the exterminating agent 13 by itself to be carried back to their colony.

Specific examples of the effective ingredient for termite extermination include organic phosphorus-based compounds such as chlorpyrifos, dichlorofenthion (ECP), diazinon, tetrachlorvinphos, pyridafenthion, fenitrothion (MEP), propetamphos, phoxim, and dichlorvos; organic halogen-based compounds such as silafluofen; carbamate-based compounds such as fenobucarb (BPMC), and propoxur; pyrethroid-based compounds such as bifenthrin, permethrin, tralomethrin, acrinathrin, and ethofenprox; neonicotinoid-based compounds such as dinotefuran, imidacloprid, and acetamiprid; insect growth regulators such as methoprene, hydroprene, pyriproxyfen, diflubenzuron, triflumuron, teflubenzuron, chlorfluazuron, flufenoxuron, hexaflumuron, and cyromazine; phenylpyrazole-based compounds such as fipronil, and pyriprole; pyrrole-based compounds such as chlorfenapyr; sulfonamide-based compounds such as amidoflumet; oxadiazole-based compounds such as metoxadiazone; and others such as hydramethylnon, boric acid, and borax. According to the type of termites as a termination target, one kind of these effective ingredients may be used solely, or two or more kinds of these effective ingredients may be used in combination. In addition to these effective ingredients, synergist, such as piperonyl butoxide, octachlorodipropylether, N-(2-ethylhexyl)-bicyclo[2.2.1]-hept-5-ene-2,3-dicarboximide, may also be used together.

The formulation of the exterminating agent 13 is not particularly limited as long as being in a solid state. Examples of the formulation include powder, granular shape, granule, tablet, lump, and capsule. The formulation of the exterminating agent 13 is particularly preferably granular-shaped formulation, granule formulation, or encapsulated formulation.

(Termite Attractant)

The termite attractant 4 is not particularly limited and may be suitably selected from among ones that the type of termites as a termination target like to feed. Examples of the termite attractant 4 include paper, wood flour, sawdust, cellulose molded articles such as cellulose particles, cotton cloth, steamed wood material and wood pieces. Hereinafter, the term "attracting termites" includes the fact that termites like to feed the termite attractant 4 and stay there.

(Termite Extermination Method)

As a termite extermination method using the termite extermination device 1, there is, for example, a method of putting the termite extermination device 1 in the ground including a termite habitat. By putting the termite extermination device 1 in the ground including the termite habitat, termites living in a deep underground colony make underground passages and termite passages from the colony, and the termites enter the attractant storage part 8 through a termite entrance 14 and feed the termite attractant 4. During the time the termites feed the termite attractant 4 or after the termites consume the termite attractant 4, the termites chew up the moisture-proof film 12 of the exterminating agent housing 3 disposed in the exterminating agent storage part 7 adjacent to an upper part of the attractant storage part 8. The termites then feed the exterminating agent 13 or contact with the exterminating agent 13, thus ensuring extermination of the termites.

The termite extermination device 1 is preferably put at depths of approximately 5 to 20 cm and at intervals of approximately 1 to 2 m. By putting the termite extermination device 1 in this manner, the locations thereof are not too deep and are easy to check, and cost savings and efficient extermination are achievable without using a number of the termite extermination devices 1 more than necessary.

In order to make it easier for termites to bite the moisture-proof film 12, the termite attractant 4 is preferably loaded in the attractant storage part 8 so as to be contacted with the moisture-proof film 12 as shown in FIG. 1(*b*). In order to ensure that termites access to the exterminating agent 13 after chewing up the moisture-proof film 12, the exterminating agent 13 is preferably loaded in the exterminating agent storage container 11 as shown in FIG. 1(*b*).

(Another Embodiment of Termite Extermination Device)

Figure 2A:
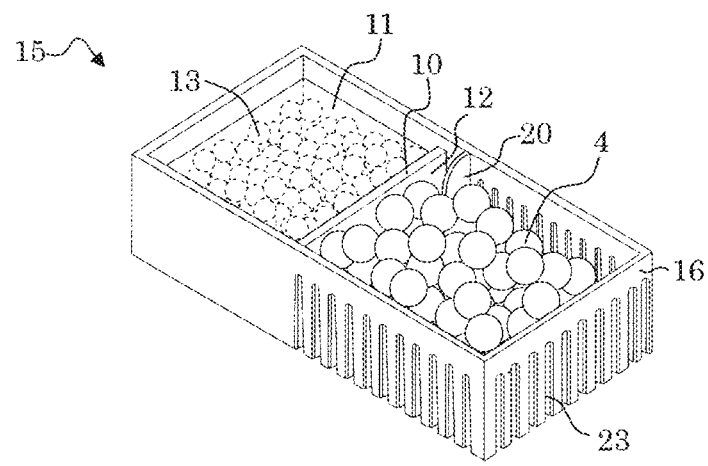
FIG. 2(a) is a perspective view showing another embodiment of the termite extermination device of the present invention (with an openable lid unshown)
Figure 2B:
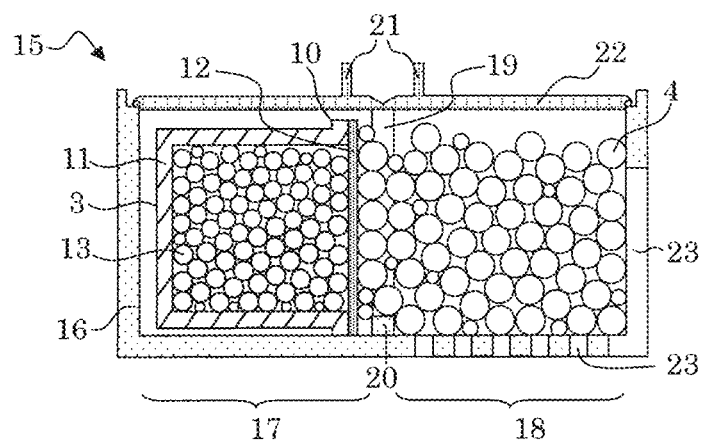
FIG. 2(b) is a cross-sectional view of the termite extermination device.

FIG. 2(*a*) is a perspective view showing a termite extermination device 15 (with an openable lid 22 unshown) as another embodiment of the termite extermination device of the present invention. FIG. 2(*b*) is a cross-sectional view of the termite extermination device 15.

The termite extermination device 15 includes a box-type attractant housing 16, and a exterminating agent housing 3 and a termite attractant 4 that are housed in the attractant housing 16. The termite extermination device 15 is similar to the termite extermination device 1 except that the attractant housing is of different type. Similar reference numerals are used to indicate similar parts.

As shown in FIG. 2(*b*), the interior of the attractant housing 16 is divided in a horizontal direction into an exterminating agent storage part 17 (exterminating agent storage space) and an attractant storage part 18 (attractant storage space) by a partition part 20 with a termite entrance 19. In the termite extermination device 15, the exterminating agent housing 3 is housed in the exterminating agent storage part 17 of the attractant housing 16, and the termite attractant 4 is housed in the attractant storage part 18. The openable lid 22 with a handle 21 is secured to an upper part of the attractant housing 16.

The exterminating agent storage part 17 is adjacent to the attractant storage part 18 in the horizontal direction, thus making it easier for termites to chew up the moisture-proof film 12.

(Termite Extermination Method)

As a termite extermination method using the termite extermination device 15, the termite extermination device 15 needs to be put in the ground or on the ground including a termite habitat.

The case of putting the termite extermination device 15 in the ground including the termite habitat is effective in exterminating termites living in an underground colony. The case of putting the termite extermination device 15 on the ground including the termite habitat is effective in exterminating termites acting in the vicinity of the surface of the earth.

The termite extermination device 15 is preferably put at depths of approximately 5 to 20 cm and at intervals of approximately 1 to 2 m. By putting the termite extermination device 15 in this manner, the locations thereof are not too deep and are easy to check, and cost savings and efficient extermination are achievable without using a number of the termite extermination devices 15 more than necessary.

In order to make it easier for termites to bite the moisture-proof film 12, the termite attractant 4 is preferably loaded in the attractant storage part 18 so as to be contacted with the moisture-proof film 12 as shown in FIG. 2(*b*). In order to ensure that termites access to the exterminating agent 13 after chewing up the moisture-proof film 12, the exterminating agent 13 is preferably loaded in the exterminating agent storage container 11 as shown in FIG. 2(*b*).

(Still Another Embodiment of Termite Extermination Device)

Figure 3:
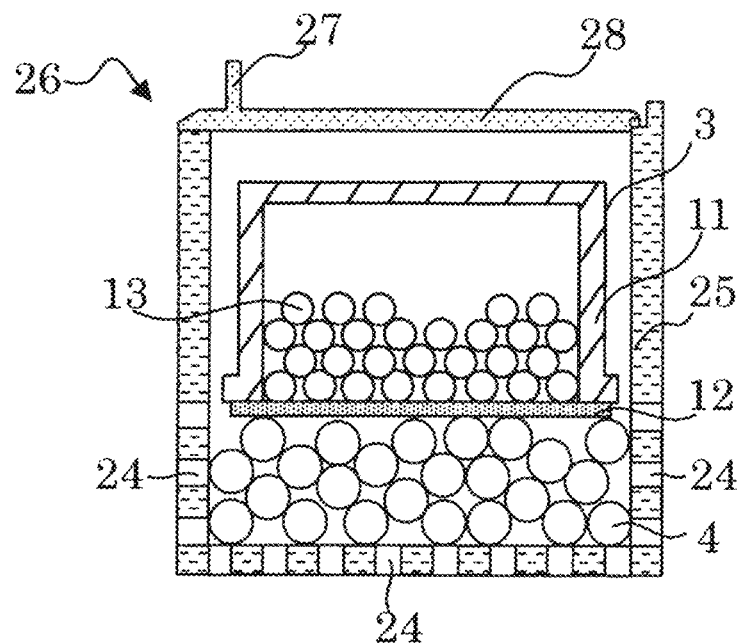
FIG. 3 is a cross-sectional view showing still another embodiment of the termite extermination device of the present invention.

The termite extermination device of the present invention is not limited to the termite extermination devices 1 and 15 as described above, and any other embodiment may be employed as long as being at least partially formed of the moisture-proof film and including the exterminating agent housing that houses therein the exterminating agent. For example, as shown in FIG. 3, the termite extermination device of the present invention may be an inexpensively-manufacturable simple termite extermination device 26 in which a termite attractant 4 is loaded in a one-box type attractant housing 25 having a termite entrance 24 at a lower part thereof, and an exterminating agent housing 3 is mounted on the termite attractant 4. Alternatively, the exterminating agent housing 3 by itself may be the termite extermination device.

The exterminating agent housing in the present invention is not limited to the foregoing exterminating agent housing 3. The exterminating agent housing is not particularly limited as long as being at least partially formed of the moisture-proof film and capable of housing therein the exterminating agent as well as having excellent water proofness and moisture proofness. For example, as shown in FIG. 4, the exterminating agent housing in the present invention may be an exterminating agent housing 29 that houses the exterminating agent 13 in the interior of a bag body formed of the moisture-proof film 12. It is also possible to employ an exterminating agent housing (not shown) including an exterminating agent storage container with a plurality of openings for termite entrances, one or a plurality of moisture-proof films fully covering the individual openings for termite entrances, and an exterminating agent housed in a closed space defined by the exterminating agent storage container and the moisture-proof film. Each of these exterminating agent housings may be used instead of the exterminating agent housing 3 disposed in the attractant housing in the foregoing termite extermination device 1, 15, or 26. Alternatively, these exterminating agent housings by themselves may be used alone as the terminate extermination device.

EXAMPLES

The present invention is specifically described below by illustrating embodiments. The present invention is, however, not limited to these embodiments.

Films each having a film structure including a PE layer as presented in Tables 1 to 3 were manufactured by an extrusion lamination method.

Films each having a film structure not including the PE layer presented in Tables 1 and 3 were manufactured by laminating individual layers with adhesive interposed therebetween.

Thereafter, the presence or absence of chewing (penetration) in the sample films was periodically observed. The results thereof are presented in Table 1. Regarding the sample film in which chewing (penetration) was observed, penetration time is indicated by the number of days elapsed when the penetration was observed, and the evaluation of penetration thereof is indicated by symbol "o". Regarding the sample film in which no penetration was observed after a period of 30 days, penetration time is indicated by symbol "–", and the evaluation of penetration is indicated by symbol "x". In the film structures in Table 1, for example, the term "paper 35" indicates a paper layer having a weighing of 35 g/m$^2$, and the term "Al6" indicates an aluminum layer with a thickness of 6 μm.

TABLE 1

| | Sample No. | Film Structure (1) | Rugging Process (2) | Penetration Time (3) | Evaluation of Penetration |
|---|---|---|---|---|---|
| | 1 | Paper 35/Al6 | Wrinkle type | 7 days | o |
| * | 2 | Paper 35/Al6 | None | — | x |
| | 3 | Paper 79.1/PE15/Al9/PET12/PE15/EAAl5 | A-type | 13 days | o |
| | 4 | Paper 79.1/PE15/Al9/PET12/PE15/EAAl5 | B-type | 4 days | o |
| * | 5 | Paper 79.1/PE15/Al9/PET12/PE15/EAAl5 | None | — | x |
| * | 6 | PE15/Al9/PET12/PE15/EAAl5 | A-type | — | x |
| * | 7 | PE15/Al9/PET12/PE15/EAAl5 | B-type | — | x |
| | 8 | Paper 79.1/PE15/Al7/PE20 | A-type | 7 days | o |
| | 9 | Paper 79.1/PE15/Al7/PE20 | B-type | 5 days | o |
| * | 10 | Paper 79.1/PE15/Al7/PE20 | None | — | x |
| * | 11 | PET12/Al7/ON15/CPP80 | A-type | — | x |
| * | 12 | PET12/Al7/ON15/CPP80 | B-type | — | x |
| * | 13 | Transparent vapor deposition PET12/ON15/CPP60 | A-type | — | x |
| * | 14 | Transparent vapor deposition PET12/ON15/CPP60 | B-type | — | x |
| * | 15 | ON15/Al40/ON15/CPP80 | A-type | — | x |
| * | 16 | ON15/Al40/ON15/CPP80 | B-type | — | x |
| * | 17 | Paper 84.9/Aluminum vapor desposition layer | B-type | 4 days | o |

Symbol "*" denotes a comparative example.

When a rugging process was applied to obtained sample films, wrinkles were added to the sample films by manual work, or the sample films were inserted into a die in order to apply the rugging process to the front and back of the sample films. FIG. 5 shows a reference photograph of a moisture-proof film subjected to the rugging process.

(Chewing Test I)

A chewing test I was conducted using a test container 30 shown in FIG. 6. That is, two plastic tubes 31a and 31b with a lid removed therefrom ("2.0 ml self-standing screw cap tube" manufactured by Watson Co., Ltd.) were used. Sawdust 32 moistened by a sprayer was loaded in the tubes 31a and 31b. Specifically, the sawdust 32 corresponding to approximately a half (1 ml) of the volume of the tube 31a was loaded in the tube 31a. The sawdust 32 was loaded in the tube 31b so as to occupy the entire volume thereof. As an air hole, a hole having a diameter of 1 mm was made at three locations on each of the right and left sides of the tube 31a. Then, 30 test insects 33 (*Reticulitermes speratus*) were loaded in the tube 31a. Subsequently, both surfaces of a sample film 34 having a structure presented in Table 1 were sandwiched between oppositely disposed tube mouths of the two tubes 31a and 31b with their respective caps removed therefrom. Both were secured to each other with a vinyl tape 35 so as to integrate the two tubes. Here, the left layer of the film structures in Table 1 (which served as the surface, namely, the outermost surface when disposed in the exterminating agent housing) was used as the side of the sample film which was adjacent to the tube storing the test insects.

(1) Regarding the thickness of the film, the thickness of a paper layer is indicated by weighing (g/m$^2$), and the thickness of another layer is indicated by μm.

The term "paper 84.9/aluminum vapor deposition layer" in sample No. 17 denotes the device in which a paper having a weighing of 84.9 g/m$^2$ was subjected to vacuum vapor deposition of aluminum. The thickness of an aluminum vapor deposition layer was 1 μm or less, which is therefore not presented.

(2) Wrinkle type: a rugged surface shape provided with wrinkles (refer to FIG. 5(*a*))

A-type: a willow-type rugged surface shape having a rugged height of approximately 0.6 mm (refer to FIG. 5(*b*)), and B-type: a stripe-type rugged surface shape having a rugged height of approximately 0.4 mm (refer to FIG. 5(*c*))

(3) The film having no penetration after the period of 30 days is indicated by symbol "–".

(Abbreviated Words)

"Al" denotes aluminum.
  "PE" denotes polyethylene.
  "PET" denotes polyethylene terephthalate.
  "EAA" denotes ethylene acrylic acid copolymer.
  "ON" denotes oriented nylon.
  "CPP" denotes cast polypropylene.

(Chewing Test II)

Figure 7:
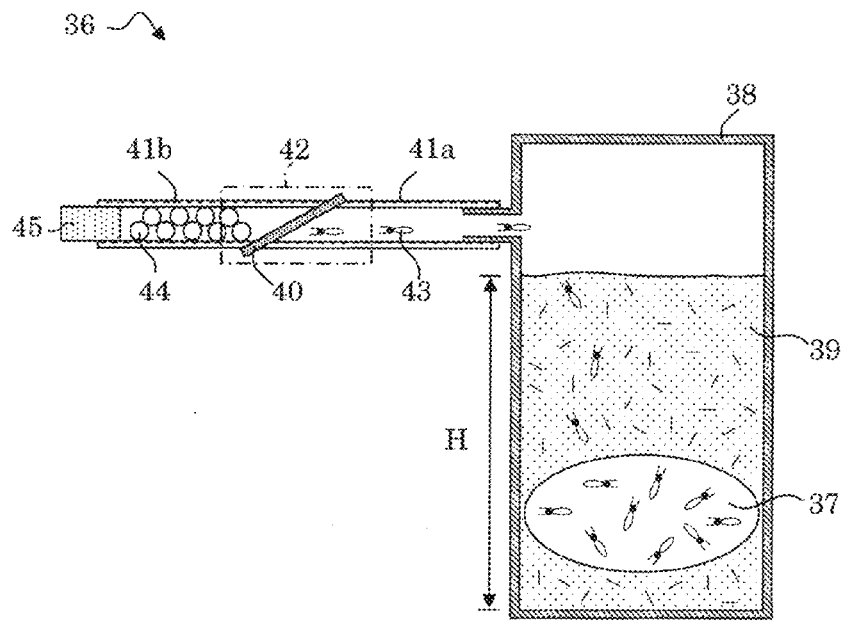
FIG. 7 is a schematic cross-sectional view of a penetration test device used for a chewing test II.

A chewing test II was conducted using a penetration test device 36 as shown in FIG. 7. A colony of *Coptotermes formosanus* 37 collected in outdoor (the height of the colony: approximately 30 to 40 cm) was put in a plastic cylindrical container 38 (with a diameter of approximately 25 cm and a height of approximately 130 cm), and soil mixed with sawdust 39 was loaded up to a height H. This was left to stand in this state for one month or more. Subsequently, both surfaces of a sample film 40 having a structure presented in Table 2 were sandwiched between oppositely disposed ends (open parts) of two polyvinyl chloride pipes 41*a* and 41*b* (with a diameter of approximately 1 cm and a length of approximately 15 cm), and were secured to each other by a clip 42, resulting in the penetration test device. One end of the pipe 41*a* was coupled to an upper side surface of the cylindrical container 38 (at a position of approximately 120 cm in height), and the presence or absence of chewing of the sample film 40 after 24 hours was observed. Here, the left layer of the film structures in Table 2 (which was the surface, namely, served as the outermost surface when disposed in the exterminating agent housing) was the side adjacent to the cylindrical container 38 storing the colony of *Coptotermes formosanus* 37. Nothing was loaded in the pipe 41*a* adjacent to the cylindrical container 38 so that *Coptotermes formosanus* 43 was free to come and go. Approximately 2 g of cellulous particles 44 as bait were loaded in the pipe 41*b*, one of the pipes sandwiching the sample film 40 therebetween. A plastic cork 45 sealed the open end of the pipe 41*b* located opposite the side at which the sample film 40 was sandwiched.

The results are presented in Table 2. In the rugging process, the film was bent by manual work so as to have a rugged surface shape provided with wrinkles. The sample film 40 was evaluated in terms of penetration as follows. That is, symbol "o" indicates the sample film 40 in which penetration was observed within a day. Symbol "x" indicates the sample film 40 in which no penetration was observed even after a day. In the present test, the entire colony of the *Coptotermes formosanus* was used as it was. There was a large population of the *Coptotermes formosanus* and they were active. Therefore, the evaluation was made according to the presence or absence of penetration after the lapse of a day.

TABLE 2

| Sample No. | Film Structure (1) | Rugging Process (2) | Evaluation of Penetration |
|---|---|---|---|
| 18 | Paper 79.1/PE15/Al9/ PET12/PE15/EAA15 | Wrinkle type | o |
| * 19 | Paper 79.1/PE15/Al9/ PET12/PE15/EAA15 | None | x |

Symbol "*" denotes a comparative example.

(1) Regarding the thickness of the film, the thickness of a paper layer is indicated by weighing (g/m$^2$), and the thickness of another layer is indicated by μm.

(2) Wrinkle type: a rugged surface shape provided with wrinkles (refer to FIG. 5(*a*))

(Abbreviated Words)
"PE" denotes polyethylene.
"Al" denotes aluminum.
"PET" denotes polyethylene terephthalate.
"EAA" denotes ethylene acrylic acid copolymer.

(Moisture Proofness Test)

A 13 g of granular silica gel was sealed in a bag of 80×80 mm formed of a sample film having a structure presented in Table 3. The bag was left to stand for one week under an environment of a temperature of 40° C. and a humidity of 75%.

The obtained change in weight (moisture content) of the granular silica gel was measured to evaluate moisture proofness. The results thereof are presented in Table 3 (The test was conducted three times for each of the sample films, and the moisture content indicates an average value of three moisture content values.). The moisture proofness was evaluated as follows. That is, symbol "o" denotes the case where the moisture content was 0.05 g or less, and symbol "x" denotes the case where the moisture content exceeded 0.05 g.

TABLE 2

| Sample No. | Film Structure (1) | Rugging Process (2) | Evaluation of Penetration |
|---|---|---|---|
| 18 | Paper 79.1/PE15/Al9/ PET12/PE15/EAA15 | Wrinkle type | o |
| * 19 | Paper 79.1/PE15/Al9/ PET12/PE15/EAA15 | None | x |

Symbol "*" denotes a comparative example.

(1) Regarding the thickness of the film, the thickness of a paper layer is indicated by weighing (g/m$^2$), and the thickness of another layer is indicated by μm.

The term "paper 84.9/aluminum vapor deposition" in sample No. 31 denotes one in which a paper having a weighing of 84.9 g/m$^2$ was subjected to vacuum vapor deposition of aluminum. The thickness of an aluminum vapor deposition layer was 1 μm or less, which is therefore not presented.

(Abbreviated Words)
"Al" denotes aluminum.
"PE" denotes polyethylene.
"PET" denotes polyethylene terephthalate.
"EAA" denotes ethylene acrylic acid copolymer.
"CPP" denotes cast polypropylene.
"PAN" denotes polyacrylonitrile.
"ON" denotes oriented nylon.
"OPP" denotes oriented polypropylene.
"OPS" denotes oriented polystyrene.
"EVOH" denotes ethylene vinyl alcohol copolymer.

(Field Test I)

A chewing test (field test I) was conducted in the open air by using the termite extermination device 15 (5.5 cm long, 10.5 cm wide, and 3.0 cm deep) as shown in FIG. 2. As a termite attractant, approximately 70 ml of cellulose particles were loaded in the attractant storage part of the termite extermination device 15. An exterminating agent not containing the effective ingredient as presented in the following Table 4 (i.e., cellulose particles, glass beads, or gelatin capsules) was loaded in the exterminating agent storage container 11 so as to fill the volume (approximately 40 ml) of the exterminating agent storage container 11. The used exterminating agent did not contain the effective ingredient in order to evaluate the present or absence of chewing of the moisture-proof film.

As the moisture-proof film 12 adhered to the flange part 10 so as to close the opening of the exterminating agent storage container 11, there was used one provided with a rugged surface shape of an approximately 0.1 mm by applying an embossing process to a moisture-proof film having a film structure made up of two layers of a paper layer (weighing: 42 g/m$^2$) and an aluminum layer (thickness: 7 μm) (refer to FIG. 5(*d*)). That is, the exterminating agent was sealed with hot-melt adhesive (ethylene-vinyl acetate copolymer based hot-melt adhesive) by using the aluminum layer of the moisture-proof film 12 as an adhesive surface (the exterminating agent side), namely, using the paper layer as the outermost surface (front surface).

The field test I was conducted by putting the termite extermination device 15 in the vicinity of a tree stump in Washuzan mountain in Okayama Prefecture at which a termite colony was found. The termite extermination device 15 was put so as to be fully buried in the ground (at an approximately 10 cm depth in the ground). Then, the presence or absence of chewing of the moisture-proof film was periodically checked during 33 days after putting the termite extermination device 15. The results thereof are presented in Table 4.

In Table 4, "the presence or absence of invasion into the device" is indicated as follows. That is, symbol "o" denotes the device in which the invasion of termites in the attractant storage part 18 was observed (including the device in which a trace of the invasion was observed), and symbol "x" denotes the device in which no invasion of termites in the attractant storage part 18 was observed, at the time of checking before the end of the test (a period of 33 days).

Regarding "evaluation of penetration," symbol "o" denotes the device in which chewing was observed, and symbol "–" denotes the unevaluable one in which no invasion of termites in the attractant storage part 18 was observed, at the time of checking before the end of the test (the period of 33 days). The number of days elapsed before the chewing is indicated by the number of days elapsed before the chewing was observed. Symbol "–" denotes the device in which no chewing was observed before the end of the period of 33 days.

applying an embossing process to a moisture-proof film having a film structure made up of two layers of a paper layer (weighing: 42 g/m$^2$) and an aluminum layer (thickness: 7 μm) (refer to FIG. 5(d)). That is, the exterminating agent was sealed with the following adhesive by using the aluminum layer of the moisture-proof film 12 as an adhesive surface (the exterminating agent side), namely, using the paper layer as the outermost surface (front surface).

Sample Nos. 43 and 44: hot-melt adhesive (ethylene-vinyl acetate copolymer based hot-melt adhesive)

Sample Nos. 45 and 46: woodworking adhesive (polyvinyl acetate emulsion adhesive)

The field test II was conducted in a forest located at Enjugahama, Gobo-city, Wakayama Prefecture. Specifically, an area near a termite hill in the forest where a termite colony was found was named as a feeding area A. Another area near a termite hill in the forest opposed to the feeding area A with the termite hill thereof interposed therebetween was named as a feeding area B. The field test II was conducted by putting the termite extermination device 15 at two places. The termite extermination device 15 was put so as to be fully buried in the ground (at an approximately 10 cm depth in the ground). Then, the presence or absence of chewing of the moisture-proof film was checked when four days were passed after putting the termite extermination device 15. The results thereof are presented in Table 5.

In Table 5, "the presence or absence of invasion into the device" is indicated as follows. That is, symbol "o" denotes the device in which the invasion of termites in the attractant

TABLE 4

| Sample No. | Exterminating Agent | Presence or Absence of invasion into the device | Evaluation of Penetration | Number of days elapsed before the chewing |
|---|---|---|---|---|
| 32 | Cellulose particles | o | o | 21 days |
| 33 | Cellulose particles | o | o | 26 days |
| 34 | Cellulose particles | o | o | 12 days |
| 35 | Cellulose particles | x | — | — |
| 36 | Glass beads | o | o | 21 days |
| 37 | Glass beads | o | o | 21 days |
| 38 | Glass beads | o | o | 33 days |
| 39 | Glass beads | x | — | — |
| 40 | Gelatin capsules | o | o | 21 days |
| 41 | Gelatin capsules | o | o | 26 days |
| 42 | Gelatin capsules | o | o | 21 days |

As presented in Table 4, the chewing of the moisture-proof film was observed in any one of the devices in which the invasion into the device was observed irrespective of the kind of the exterminating agent (Sample Nos. 32-34, 36-38, and 40-42).

(Field Test II)

A chewing test (field test II) was conducted in the open air by using the termite extermination device 15 (5.5 cm long, 10.5 cm wide, and 3.0 cm deep) as shown in FIG. 2. As a termite attractant, approximately 70 ml of cellulose particles were loaded in the attractant storage part of the termite extermination device 15. An exterminating agent, approximately 40 ml of cellulose particles were loaded in the exterminating agent storage container. The used exterminating agents did not contain the effective ingredient in order to evaluate the present or absence of chewing of the moisture-proof film.

As the moisture-proof film 12 adhered to the flange part 10 so as to close the opening of the exterminating agent storage container 11, there was used one provided with a rugged surface shape of an approximately 0.1 mm by storage part 18 was observed (including the device in which a trace of the invasion was observed) at the time of checking.

Regarding "evaluation of penetration, symbol "o" denotes the device in which the chewing was observed at the time of checking.

TABLE 5

| Sample No. | Placement Locations of the device | Presence or Absence of invasion into the device | Evaluation of Penetration |
|---|---|---|---|
| 43 | Feeding Area A | o | o |
| 44 | Feeding area B | o | o |
| 45 | Feeding area B | o | o |
| 46 | Feeding area B | o | o |

In the field test II, the termite extermination device 15 was dug out and recovered when four days passed after putting the device. As a result, the chewing of the moisture-proof film was observed in all the samples in a period of time as short as the four days.

Figure 8:
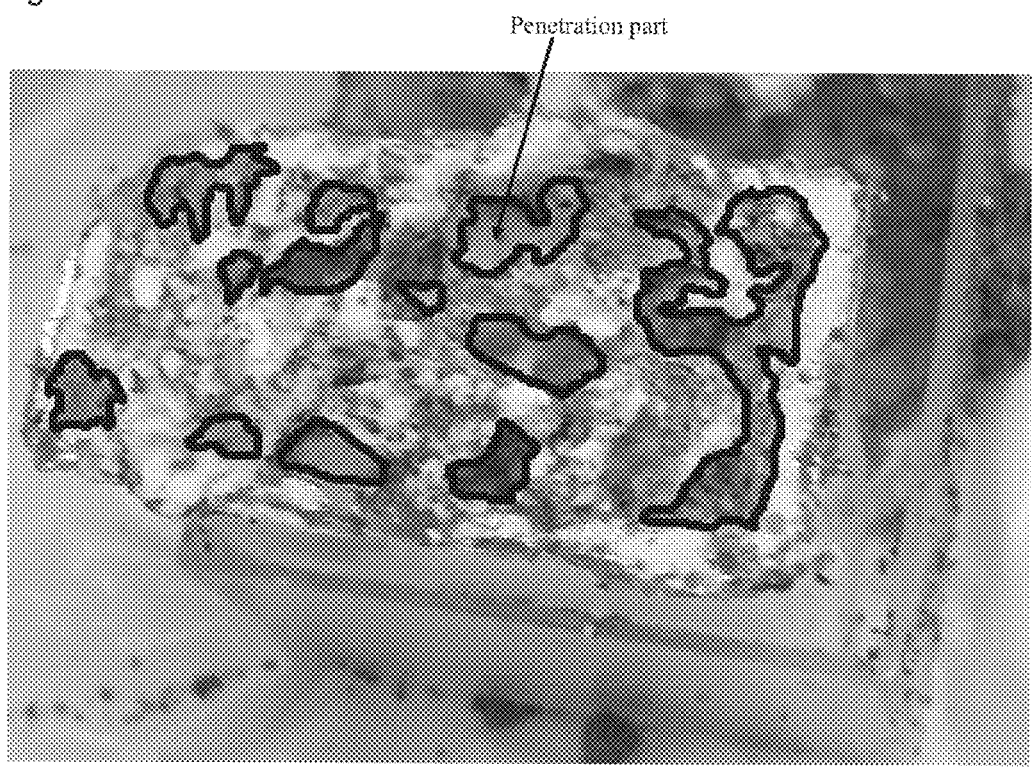
FIG. 8 is a photograph of the surface of a moisture-proof film in sample No. 43 after a field test II.

FIG. 8 shows a state of the moisture-proof film (sample No. 43) after the field test II, which was chewed by termites. As indicated by surrounded regions in FIG. 8, the paper layer and the aluminum layer of the moisture-proof film were generally chewed and were penetrated. Further, termite passages were formed in the cellulose particles loaded in the exterminating agent housing.

(Field Test III)

A chewing test (field test III) was conducted in the open air by using the termite extermination device 1 (in which the exterminating agent storage part 7 had a diameter of approximately 6 cm and a height of 2 cm, and the attractant storage part 8 had a height of 10 cm) as shown in FIG. 1, and the termite extermination device 15 (5.5 cm long, 10.5 cm wide, and 3.0 cm deep) as shown in FIG. 2. As a termite attractant, approximately 40 ml of cellulose particles were loaded in the attractant storage part of the termite extermination device 1, and approximately 70 ml of cellulose particles were loaded in the attractant storage part of the termite extermination device 15. As an exterminating agent, approximately 40 ml of sawdust moistened by a sprayer were loaded in each of the exterminating agent storage containers of the termite extermination devices 1 and 15. The used exterminating agent did not contain the effective ingredient in order to evaluate the present or absence of chewing of the moisture-proof film.

As the moisture-proof film 12 thermally welded to the flange part 10 so as to close the opening of the exterminating agent storage container 11, the moisture-proof film having a film structure presented in Table 6 was used. That is, the exterminating agent was sealed so that the left layer of the moisture-proof film 12 in the film structure presented in Table 6 served as the outermost surface.

The field test III was conducted by putting the termite extermination devices 1 and 15 in the vicinity of a tree stump in Washuzan mountain in Okayama Prefecture at which a termite colony was found. The termite extermination device 1 was put so as to be buried in the ground (at an approximately 10 cm depth in the ground). The termite extermination device 15 was put so as to be fully buried in the ground (at an approximately 10 cm depth in the ground). Then, the presence or absence of chewing of the moisture-proof film was checked when 11 days or 43 days passed after putting the device. The chewing of the moisture-poof film was observed in both of the termite extermination devices. The results thereof are presented in Table 6.

Regarding "evaluation of penetration" in Table 6, symbol "o" denotes the device in which the chewing was observed at the time of checking.

(3) B-type: a stripe-type rugged surface shape having a rugged height of approximately 0.4 mm (refer to FIG. 5(c))

(Abbreviated Words)

"PE" denotes polyethylene.
"Al" denotes aluminum.
"PET" denotes polyethylene terephthalate.
"EAA" denotes ethylene acrylic acid copolymer.
"CPP" denotes cast polypropylene.

The invention claimed is:

1. A termite extermination device comprising:
an attractant housing including an attractant storage part that houses therein a termite attractant,
an exterminating agent housing that is housed in the attractant housing and houses an exterminating agent in an interior of the exterminating agent housing, wherein the exterminating agent housing is disposed adjacent to the attractant storage part,
a moisture-proof film closing an opening of the exterminating agent housing, wherein the moisture-proof film comprises a laminate comprising a paper layer and a metal layer laminated one upon another, at least the paper layer having a rugged surface shape,
wherein the laminate is disposed at the opening of the exterminating agent housing so that the paper layer serves as an outermost surface of the laminate with respect to the exterminating agent housing, and
wherein the moisture-proof film faces to the attractant storage part.

2. A termite extermination method comprising putting a termite extermination device at a termite habitat,
wherein the termite extermination device comprises an attractant housing including an attractant storage part that houses therein a termite attractant, an exterminating agent housing that is housed in the attractant housing and houses an exterminating agent in an interior of the exterminating agent housing, and a moisture-proof film closing an opening of the exterminating agent housing,
wherein the moisture-proof film comprises a laminate comprising a paper layer and a metal layer laminated one upon another, at least the paper layer having a rugged surface shape,
wherein the laminate is disposed at the opening of the exterminating agent housing so that the paper layer serves as an outermost surface of the laminate with respect to the exterminating agent housing, and
wherein the exterminating agent housing is disposed adjacent to the attractant storage part, and

TABLE 6

| Sample No. | Termite Extermination Device (1) | Film Structure (2) | Rugging Process (3) | Placement Period of the device | Evaluation of Penetration |
|---|---|---|---|---|---|
| 47 | Stake-type | Paper 79.1/PE15/Al9/PET12/PE15/EAA15 | B-type | 43 days | o |
| 48 | Box-type | Paper 79.1/PE15/Al9/PET12/PE15/EAA15 | B-type | 43 days | o |
| 49 | Box-type | Paper 79.1/PE15/Al9/PET12/CPP30 | B-type | 11 days | o |

(1) Stake-type: the termite extermination device shown in FIG. 1

Box-type: the termite extermination device shown in FIG. 2

(2) Regarding the thickness of the film, the thickness of a paper layer is indicated by weighing (g/m$^2$), and the thickness of another layer is indicated by μm.

wherein the moisture-proof film faces to the attractant storage part.

3. The termite extermination method according to claim 2, wherein the laminate further comprises a synthetic resin layer.

4. The termite extermination method according to claim 2, wherein the moisture-proof film comprises the paper layer placed on top of a first synthetic resin layer placed on top of the metal layer placed on top of a second synthetic resin layer.

5. The termite extermination method according to claim 4, wherein at least one of the first synthetic resin layer and the second synthetic resin layer is a hardly-stretchable resin film.

6. The termite extermination method according to claim 2, wherein the moisture-proof film has a thickness of 5 to 500 micrometers.

7. The termite extermination method according to claim 2, wherein the attractant housing comprises a stake-type housing.

* * * * *